(12) United States Patent
Park et al.

(10) Patent No.: US 10,353,033 B2
(45) Date of Patent: Jul. 16, 2019

(54) METHOD FOR QUANTITATIVE ANALYSIS

(71) Applicant: LG Chem, Ltd., Seoul (KR)

(72) Inventors: Hee Yong Park, Daejeon (KR); Soo Young Kwak, Daejeon (KR); Hye Sung Cho, Daejeon (KR)

(73) Assignee: LG Chem, Ltd. (KR)

( * ) Notice: Subject to any disclaimer, the term of this patent is extended or adjusted under 35 U.S.C. 154(b) by 215 days.

(21) Appl. No.: 15/433,048

(22) Filed: Feb. 15, 2017

(65) Prior Publication Data

US 2017/0315190 A1    Nov. 2, 2017

(30) Foreign Application Priority Data

May 2, 2016   (KR) .................. 10-2016-0054142

(51) Int. Cl.
*G01R 33/46* (2006.01)
*G01N 24/08* (2006.01)

(52) U.S. Cl.
CPC ......... *G01R 33/4625* (2013.01); *G01N 24/08* (2013.01)

(58) Field of Classification Search
CPC .......... G01R 33/4625; G01R 33/4816; 4G01R 33/46; G01R 33/485; G01N 24/08; G01N 24/082; G01N 24/00
See application file for complete search history.

(56) References Cited

U.S. PATENT DOCUMENTS

| | | |
|---|---|---|
| 7,804,298 B2 | 9/2010 | Miura et al. |
| 9,285,444 B2 | 3/2016 | Huber et al. |
| 2006/0223191 A1 | 10/2006 | Harutyunyan et al. |
| 2009/0033325 A1 | 2/2009 | Miura et al. |
| 2015/0042328 A1 | 2/2015 | Huber et al. |
| 2018/0143148 A1* | 5/2018 | May ................. G01N 24/08 |

FOREIGN PATENT DOCUMENTS

| | | |
|---|---|---|
| JP | 2010060511 A | 3/2010 |
| JP | 4555294 B2 | 9/2010 |
| JP | 5027798 B2 | 9/2012 |
| JP | 5945365 B2 | 7/2016 |
| KR | 100864561 B1 | 10/2008 |
| KR | 20100133717 A | 12/2010 |

OTHER PUBLICATIONS

Schönberger, T., et al. "Guide to NMR method development and validation—Part I: Identification and quantification." Eurolab Technical Report Jan. 2014 (2014). (Year: 2014).*
Hu, Weiguo "Converting signal area ratio to molar and weight ratio." UMass Nuclear Magnetic Resonance (NMR) Labs. Mar. 20, 2013, <https://blogs.umass.edu/weiguoh/?p=266> (Year: 2013).*

(Continued)

*Primary Examiner* — Rishi R Patel
(74) *Attorney, Agent, or Firm* — Lerner, David, Littenberg, Krumholz & Mentlik, LLP

(57) ABSTRACT

The present invention provides a method for quantitative analysis of a compound in a sample characterized in that the quantitative analysis is performed by a method of using an external standard which obtains NMR spectra of a sample and a standard substance and then compares them, and it can be applied even to an insoluble sample.

4 Claims, 6 Drawing Sheets

(56) References Cited

OTHER PUBLICATIONS

Malz, Frank, and Harald Jancke. "Validation of quantitative NMR." Journal of pharmaceutical and biomedical analysis 38.5 (2005): 813-823. (Year: 2005).*
Chen, Li-Shi et al., "Calibration of solid state NMR carbon structural parameters and application in coal structure analysis", Journal of Fuel Chemistry and Technology, Oct. 2017, vol. 45, No. 10, pp. 1153-1163 (Abstract Only).
Dybowski, C. et al., "Solid-State NMR Spectroscopy", Analytical Chemistry, Jun. 12, 2008, vol. 80, No. 12, pp. 4295-4300.
Glatfelter, A. et al., "Quantitative determination of lead in mixtures of lead (II) halides using solid-state 207Pb NMR spectroscopy", The Analyst, The Royal Society of Chemistry, Jul. 11, 2006, vol. 131, pp. 1207-1209.
Han, Oc Hee, et al., "Sampling Methods for Quantification of Solid-state Phases in Powder Samples with Solid-state NMR Spectroscopy." Bull. Korean Chem. Soc., 2009, vol. 30, No. 5., pp. 1077-1079.
Yang, Woon Seok, et al., "High-performance photovoltaic perovskite layers fabricated through intramolecular exchange." Science 2015, vol. 348, No. 6240, pp. 1234-1237. Downloaded from www.sciencemag.org on May 21, 2015.

* cited by examiner

METHOD FOR QUANTITATIVE ANALYSIS

CROSS-REFERENCE TO RELATED APPLICATION

This application claims the benefit of Korean Patent Application No. 10-2016-0054142 on May 2, 2016 with the Korean Intellectual Property Office, the disclosure of which is herein incorporated by reference in its entirety.

TECHNICAL FIELD

The present invention relates to a method for quantitative analysis of a sample using an NMR spectrum.

BACKGROUND OF ART

Soluble samples can be quantitatively analyzed by various methods. As an example, the samples can be analyzed based on spectroscopic detection (e.g., UV/Vis, ELSD, etc.) or spectral detection (e.g., mass spectrometer) after performing chromatographic separation. NMR is most frequently used for the analysis of chemical structure, but it is also considered important for quantitative analysis gradually. NMR can be used for quantitative analysis because the integrated intensity of a signal is directly proportional to the number of nuclei displayed on the signal. In addition, since the sensitivities of all the protons in the spectrum are the same, there is an advantage that no extinction coefficient or verification/calibration is required for quantitative analysis.

The method most frequently used in the quantitative analysis using NMR is a method using the internal standard. In other words, it is a method in which a standard substance which knows its molecular structure and used amount is put together in a sample, and the integrated intensities of the respective signals are compared and quantitatively analyzed. This method has an advantage that the quantitative analysis is simple and accurate, but there is a disadvantage that it cannot be applied to an insoluble sample.

In the case of the insoluble sample, SSNMR (solid state NMR) can be applied, but there is a limit to the quantitative analysis using the internal standard. The reasons for this are as follows: 1) the internal standard and the sample should be uniformly mixed, but in the case of the insoluble sample, the uniform mixing is difficult; 2) the standard substance or the sample remains in the mixing tool during the mixing process and thus, accurate quantitative analysis is difficult; 3) a spinning error occurs due to nonuniform mixing; and 4) NMR peak appears broadly, and thus it is difficult to select an internal standard that can be distinguished from samples.

Recently, researches on inorganic and inorganic composite substances and inorganic substances have been actively conducted. However, since most of these substances are insoluble substances, a method of quantifying the same is required. However, in a conventional quantitative analysis of such insoluble substances, a method such as TGA or the like has been used, but there was problems that the reliability is lowered, the method of quantitative analysis is complicated, and a lot of time is required.

Therefore, the present inventors have conducted intensive studies on a method for quantitative analysis of samples, particularly a method for quantitative analysis of insoluble samples. As a result, they have found that the quantitative analysis is performed by using an external standard method that obtains NMR spectra of a sample and a standard substance and then compare them as will be described later, wherein samples can be quantitatively analyzed from information of the respective NMR spectra. The present invention has been completed on the basis of such finding.

DETAILED DESCRIPTION OF THE INVENTION

Technical Problem

It is an object of the present invention to provide a method for quantitative analysis of a sample using an NMR spectrum.

Technical Solution

In order to achieve the above object, the present disclosure provides a method for quantifying a compound in a sample comprising the steps of:

1) obtaining NMR spectrum of NMR active atom of a standard substance containing the NMR active atom contained in the compound, and NMR spectrum of the NMR active atom of the compound under the same condition;

2) obtaining FID (free induction decay) amplification values of characteristic peaks in the NMR spectrum of the standard substance and the NMR spectrum of the sample, respectively; and 3) comparing the respective FID amplification values to measure the concentration of the compound in the sample.

The present invention is for quantitative analysis of a specific compound contained in a sample and is characterized by quantifying it using an NMR spectrum. Unless stated otherwise herein, a compound in a sample means a compound to be quantitatively analyzed as a compound contained in the sample. In particular, as the sample and the compound contained therein, not only a soluble substance but also an insoluble substance can be used.

In general, because the integrated intensity of a signal in a NMR spectrum is proportional to nuclides displayed on the signal, quantification can be performed based on the specific signal of the compound to be quantified. In other words, when a standard substance that knows its molecular structure is put together in a sample for accurate quantitative analysis, the integrated intensity of a signal of a standard substance in a NMR spectrum, and the integrated intensity of a specific signal of a compound to be quantified can be obtained. In this case, since the molecular structure and the amount of the standard substance are known, quantitative analysis of a compound in the sample is possible. Thus, the standard substance that is put together with the sample is referred to as an "internal standard".

However, the quantitative analysis as described above has a problem that it is difficult to apply to an insoluble sample. The most important reason is that, in order to obtain a significant NMR spectrum, the sample and the standard substance should be mixed uniformly, but in the case of the insoluble sample it is not mixed in a solvent, and so it is difficult to mix uniformly.

In this regard, the present invention uses a method for using a method for obtaining NMR spectra of the standard substance and the sample separately and then analyzing them, rather than mixing the standard substance with the sample as described above, and the standard substance used herein is referred to as an "external standard".

Hereinafter, the present invention will be described in detail for each step.

Step 1 of the present invention is a step of obtaining NMR spectra of a standard substance and a sample, respectively.

Because of obtaining the respective NMR spectra and comparing them, the compound contained in the sample and standard substance must contain the same NMR active atoms. The NMR active atom may be, for example, hydrogen, lithium, carbon, fluorine, silicon, phosphorus, lead, or tin.

NMR spectra of the sample and the standard substance are obtained on the basis of the NMR active atom. For example, when $^{13}C$ is used as a reference, $^{13}C$ NMR is obtained for each of the sample and the standard substance. In addition, the NMR spectrum referred to in the present invention includes SSNMR (solid state NMR). For example, when the NMR active atom is set to $^{207}Pb$, $^{207}Pb$ SSNMR is obtained for each of the sample and the standard substance. Further, since quantitative analysis is performed by obtaining the NMR spectra of the sample and the standard substance and comparing them, the conditions for obtaining the NMR spectrum should be the same. The above condition means a condition necessary for NMR measurement, and for example, it means that, when performing NMR measurement, the number of scans, the delay time, the pulse width, the pulse power, the receiver gain, and the spinning rate are the same. Further, the range of each condition is not limited as long as it is suitable for obtaining the respective NMR spectra under the same condition.

On the other hand, in the case of a standard substance, since it is possible to know its molecular structure, molecular weight, and mass used to obtain the NMR spectra, quantitative analysis can be performed while utilizing them later. Further, in the case of the standard substance, its type is not particularly limited as long as a characteristic peak appears in the NMR spectrum, and preferably, a substance in which a characteristic peak appears prominently in the NMR spectrum is used. For example, when obtaining a $^{13}C$ NMR spectrum, the standard substance is preferably HMB (hexamethylbenzene), and when obtaining $^{207}Pb$ NMR spectrum, the standard substance is preferably $Pb(NO_3)_2$.

Step 2 of the present invention is a step of obtaining FID amplification values of characteristic peaks in each of the NMR spectra obtained in Step 1 above.

The NMR spectrum is based on the free induction decay (FID) which is an electrical signal observed in a magnetic field. Since the FID itself is difficult to analyze, it is converted into a spectrum. In this process, a phase adjustment, a baseline correction, and a peak integration are performed. In the NMR spectrum, the integrated intensity of a specific peak is directly proportional to the number of nuclei appearing at the peak, and so this can be used for quantitative analysis. However, when many peaks are overlapped in the NMR spectrum, it is difficult to derive the integrated intensity and thus quantitative analysis is difficult.

However, conversely, the FID can be extracted at a specific peak region of the NMR spectrum. In this case, the FID amplification values can be extracted. These FID amplification values contain quantitative information on specific peaks in the NMR spectrum, and therefore quantitative analysis is possible by extracting it. The FID amplification value can be obtained, for example, using Agilent's Vnmrj 4.2 software.

That is, the FID amplification value in a specific peak region of the NMR spectrum of the standard substance is directly proportional to the amount of the nuclide displayed at the peak, and the NMR spectrum of the sample is obtained under the same condition as the NMR spectrum of the standard substance, and the above proportional relationship can be applied even to the FID amplification value of the sample. Therefore, if the FID amplification value is obtained on the basis of the specific peak of the compound to be quantified from the NMR spectrum of the sample, it is possible to quantitatively analyze the compound by comparing it with the FID amplification value of the standard substance.

Step 3 of the present invention is a step of analyzing the concentration of the compound in the sample from each of the FID amplification values obtained in Step 2 above.

In Step 2 above, if the FID amplification values of the characteristic peak are obtained from the NMR spectrum of the standard substance, the molecular structure of the standard substance and the used amount thereof are known and so quantitative analysis is possible based on the values thereof.

Specifically, each FID amplification value is proportional to the number of NMR active atoms of a standard substance or a compound in the sample. Therefore, the concentration of the compound in the sample can be measured by comparing the FID amplification values as shown in Equation (1) below.

$$\text{Concentration of compound in sample (wt \%)} = (A/B) \times (C/D) \times (E/F) \times (G/H) \quad \text{[Equation 1]}$$

in the Equation 1,

A is the number of NMR active atoms in a molecular of a standard substance corresponding to the characteristic peak of the standard substance, B is the number of NMR active atoms in a molecular of a compound corresponding to the characteristic peak of the sample, C is the molecular weight of the compound, D is the molecular weight of the standard substance, E is the mass of the standard substance used to obtain the NMR spectrum of the standard substance, F is the mass of the sample used to obtain the NMR spectrum of the sample, G is the FID amplification value of the sample, and H is the FID amplification value of the standard substance.

In the Equation 1, A to F are values that can be obtained before obtaining NMR spectra, and G and H are values that can be obtained through Steps 1 and 2 described above.

As an example, in the case of Example 1 to be described later, a $^{13}C$ NMR spectrum was obtained under the same condition using HMB (hexamethylbenzene) as a standard substance and using a mixture of HMB and ADM (adamantane) as a sample and then HMB was quantitatively analyzed by extracting the FID amplification value of the peak of each methyl group. As a result, quantitative analysis almost equal to the actual value was possible.

Further, in the case of Example 2 to be described later, a $^{207}Pb$ NMR spectrum was obtained under the same condition using $Pb(NO_3)_2$ as a standard substance and using a mixture of $PbI_2(DMSO)$ and $PbI_2$ as a sample, and then FID amplification values of the respective Pd peaks were extracted and quantitatively analyzed. As a result, the quantitative analysis almost equal to the value verified by TGA was possible.

As described above, in the present invention, after obtaining the NMR spectrum by the method using the external standard, it is possible to quantitatively analyze a compound in the sample from information thereon, and it can also be applied to a soluble sample as well as an insoluble sample.

Advantageous Effects

The present invention provides a method for quantitative analysis of a compound in a sample characterized in that the quantitative analysis is performed by a method of using an external standard which obtains NMR spectra of a sample and a standard substance and then compares them, and it can be applied even to an insoluble sample.

DETAILED DESCRIPTION OF THE EMBODIMENTS

Hereinafter, preferred examples will be presented to aid in understanding of the present invention. However, the following examples are provided for illustrative purposes only, and the content of the present invention is not limited by these Examples.

In the following Examples, unless stated otherwise, the NMR spectrum used Agilent DD2 600 MHz SSNMR (using a 1.6 mm SSNMR probe) and the FID amplification values were obtained using Agilent's Vnmrj 4.2 software.

Example 1: Quantification of HMB in a Sample

In order to verify the quantification method according to the present invention, experiments were conducted using HMB (hexamethylbenzene) and ADM (adamantane). Samples of HMB 50 (ADM:HMB=50:50 (wt %)) and HMB 30 (ADM:HMB=70:30 (wt %)) were prepared, respectively, using HMB (HMB 100 wt %) with the external standard. The external standard sampled in the NMR rotor was 19.48 mg, while HMB 50 and HMB 30 were 19.89 mg and 19.88 mg, respectively.

Figure 1:
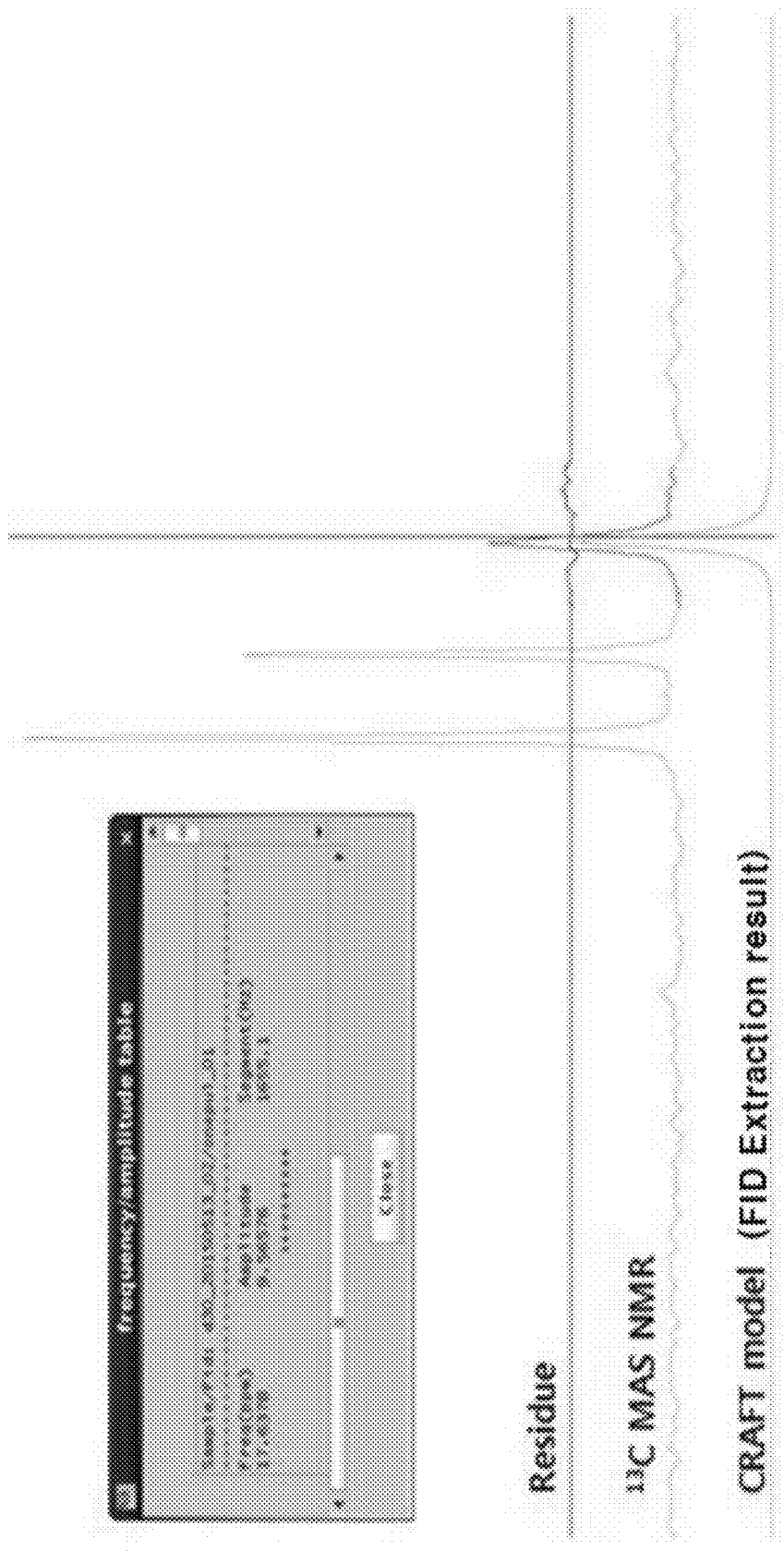
FIG. 1 shows the extraction result of the FID amplification value for HMB 50 sample in Example 1 of the present invention.

For each of them, NMR spectra were obtained under the following conditions, and FID amplification values were respectively extracted for characteristic peaks corresponding to a methyl group of HMB. At this time, the delay time was changed to 1 sec, 5 sec and 30 sec, respectively, and experiments were conducted.

pulse width=90 degree pulse
number of scans=16
receiver gain=24
spinning rate=10 kHz An example of the extraction result of FID amplification value for HMB 50 is shown in FIG. 1, and the extraction result of FID amplification value for the remaining samples and their quantitative results are shown in Table 1 below.

TABLE 1

| | Delay time = 1 sec | | Delay time = 5 sec | | Delay time = 30 sec | |
|---|---|---|---|---|---|---|
| | FID amplification value | Quantitative value(wt %) | FID amplification value | Quantitative value(wt %) | FID amplification value | Quantitative value(wt %) |
| External standard | 14.0 | — | 19.1 | — | 18.5 | — |
| HMB 50 | 6.5 | 45.5 | 8.2 | 42.0 | 9.6 | 50.6 |
| HMB 30 | 4.9 | 34.6 | 6.8 | 34.9 | 5.9 | 31.2 |

In Table 1 above, the quantitative value was calculated using Equation 1 described above. For example, in the case of HMB 50 at a delay time=30 sec, when substituted into Equation 1 described above, the quantitative value is as follows.

$$\text{Quantitative value (wt \%)} = (A/B) \times (C/D) \times (E/F) \times (G/H)$$

A (the number of methyl group in HMB molecule)=6
B (the number of methyl group in HMB molecule)=6
C (HMB molecular weight)=162.28 g/mol
D (HMB molecular weight)=162.28 g/mol
E (mass of sampled external standard in NMR rotor)=19.48 mg
F (mass of sampled HMB 50 in NMR rotor)=19.89 mg
G (FID amplification value of external standard)=18.5
H (FID amplification value of HMB 50)=9.6

As described above, it could be confirmed that the quantitativeness was improved with sufficient delay time, and an error was not large.

Example 2: Quantification of PbI$_2$(DMSO)$_2$ in a Sample

1) Preparation of Sample

An example of using a DMSO adduct (PbI$_2$(DMSO)$_2$) as a perovskite precursor in order to produce perovskite used as a light absorber of a solar cell has been reported (Science 2015, Vol. 348, no. 6240, pp. 1234-1237). According to this literature, PbI$_2$ was dissolved in DMSO to produce an intermediate, which was then heated to produce PbI$_2$(DMSO). However, the intermediates mentioned above was mixed in (PbI$_2$(DMSO)$_2$) and PbI$_2$(DMSO), and the range of each content varies depending on the production conditions. In order to produce PbI$_2$(DMSO) with high purity, it is necessary to confirm the concentration of PbI$_2$(DMSO)$_2$ in the intermediate.

Thus, according to the above document, PbI$_2$ (50 g) was dissolved in 150 mL of DMSO at 60° C., and then 350 mL of toluene was added dropwise. Subsequently, the precipitate was filtered and dried for 3 hours, and a portion thereof was taken as a 'first sample'. The remaining samples except for the first sample were placed in a vacuum oven at 60° C.

for 24 hours to prepare PbI$_2$(DMSO), and a portion thereof was taken as a 'second sample'.

2) Selection of Characteristic Peaks

Figure 2:
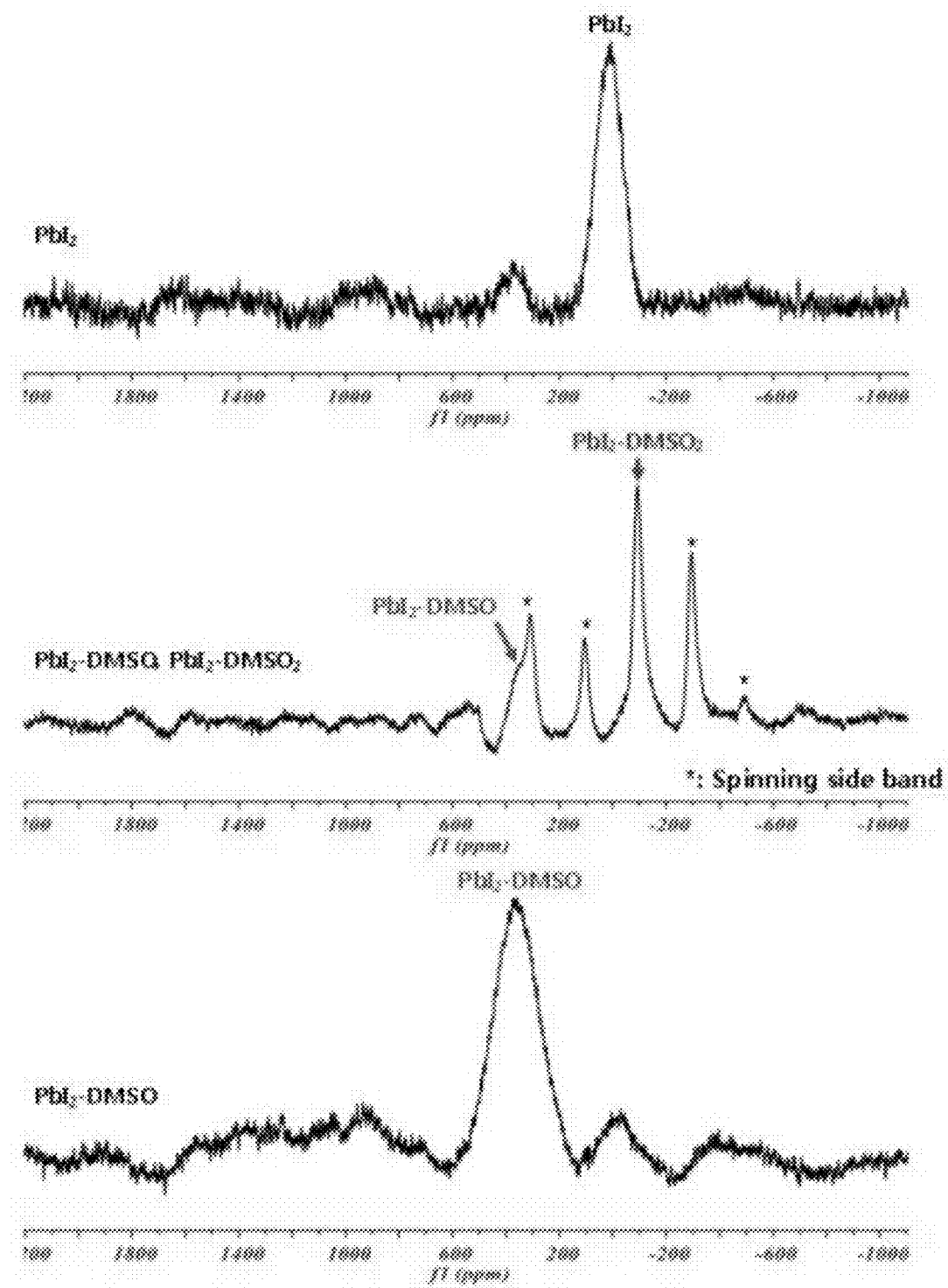
FIG. 2 shows a $^{207}$Pb SSNMR spectrum for PbI$_2$, a first sample, and a second sample in Example 2 of the present invention.

In order to select the characteristic peaks of PbI$_2$(DMSO)$_2$ and PbI$_2$(DMSO) in the first sample and the second sample, $^{207}$Pb SSNMR spectrum was obtained for PbI$_2$, a first sample and a second sample used in the above preparation under the following conditions using a 3.2 mm SSNMR probe at Agilent DO 2600 MHz, and the results are shown in FIG. 2.

pulse power (tpwr)=55
pulse width (pw)=5.00 usec
ax90=3500
delay time=5 sec
number of scans=50000
receiver gain=60
spinning rate=25 kHz As shown in FIG. 2, PbI$_2$(DMSO)$_2$ and PbI$_2$(DMSO) were present in the first sample, and the peak of PbI$_2$(DMSO)$_2$ was taken as a characteristic peak. Also, PbI$_2$(DMSO)$_2$ and PbI$_2$(DMSO) were present in the second sample, and the peak of PbI$_2$(DMSO) was taken as a characteristic peak.

3) Extraction of FID Amplification Value of Standard Substance

Figure 3:
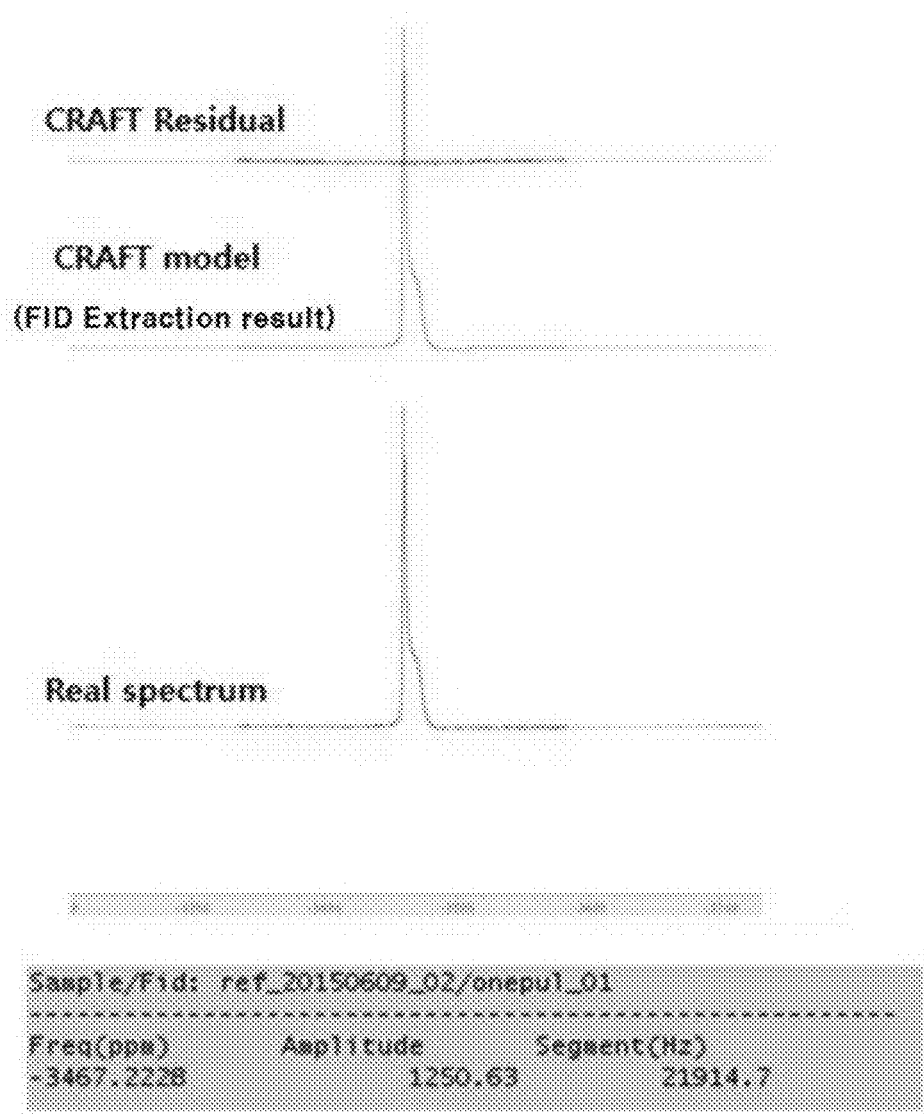
FIG. 3 shows a $^{207}$Pb SSNMR spectrum of Pb(NO$_3$)$_2$ in Example 2 of the present invention.
Figure 4:
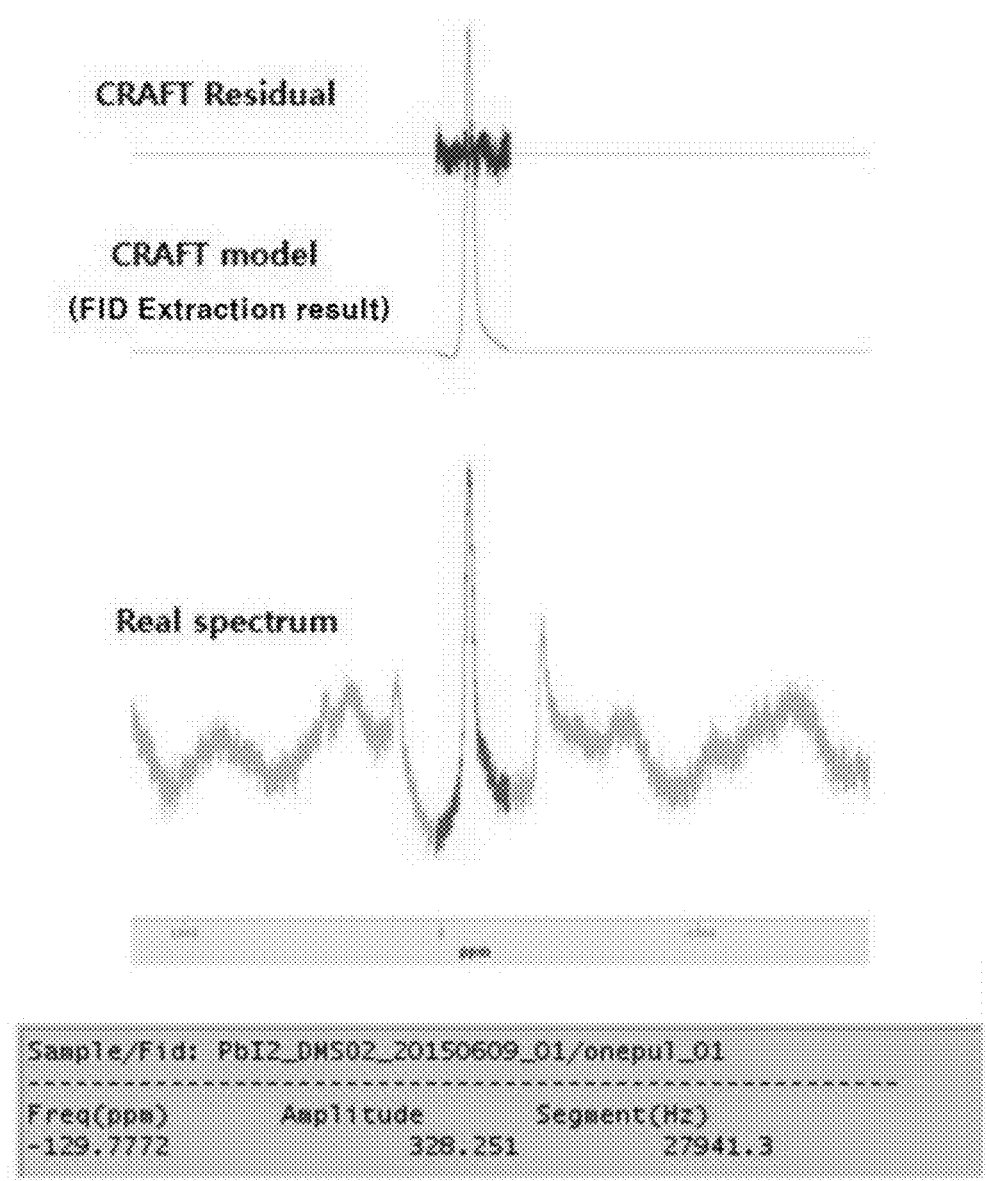
FIG. 4 shows the extraction result of FID amplification value for the characteristic peak of PbI$_2$(DMSO)$_2$ in Example 2 of the present invention.

Then, Pb(NO$_3$)$_2$, (Pb(NO$_3$)$_2$ 100 wt %, 32 mg) were used as $^{207}$Pb standard (external standard). $^{207}$Pb SSNMR spectrum was obtained under the following conditions using Agilent DD2 600 MHz SSNMR (using a 1.6 mm SSNMR probe). The FID amplification value of the characteristic peak of Pb was extracted from the NMR spectrum of Pb(NO$_3$)$_2$, and the result is shown in FIG. 3.

pulse power(tpwr)=60
pulse width(pw)=90 degree pulse (2.25 usec)
ax90=3500
delay time=5 sec
number of scans=5000
receiver gain=60
spinning rate=35 kHz 4) Quantification of PbI$_2$(DMSO)$_2$ in a First Sample $^{207}$Pb SSNMR spectrum was obtained under the same condition as in 3) above using 21.98 mg of the first sample. In the above spectrum, the HD amplification value of the characteristic peak of PbI$_2$(DMSO)$_2$ confirmed previously was extracted and the result is shown in FIG. 4.

Using the above results, PbI$_2$(DMSO)$_2$ in the first sample was quantified as shown in Table 2 below.

TABLE 2

| | |
|---|---|
| (C) Molecular weight of PbI$_2$(DMSO)$_2$ | 617.27582 (g/mol) |
| (D) Molecular weight of Pb(NO$_3$)$_2$ | 331.21 (g/mol) |
| (E) Mass of Pb(NO$_3$)$_2$ | 32 mg |
| (F) Mass of the first sample | 21.98 mg |
| (G) FIF Amplification value of the first sample | 328.521 |
| (H) FID amplification value of Pb(NO$_3$)$_2$ | 1250.63 |

Concentration of PbI$_2$(DMSO)$_2$ in the first sample ((C/D) × (E/F) × (G/H)) = 71.2(wt %)

Figure 5:
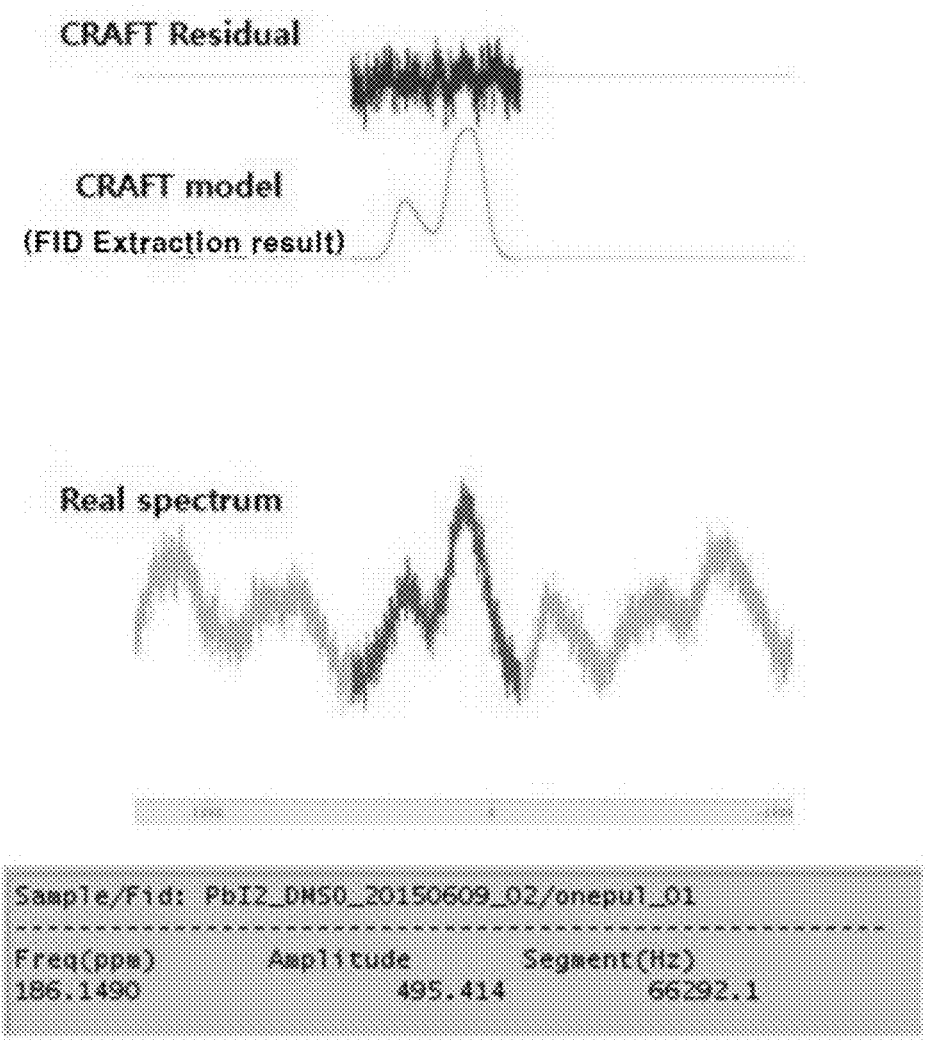
FIG. 5 shows the extraction result of the FID amplification value for the characteristic peak of PbI$_2$(DMSO) in Example 2 of the present invention.

5) Quantification of PbI$_2$(DMSO)$_2$ in a Second Sample $^{207}$Pb SSNMR spectrum was obtained under the same condition as in 3) above using 21.36 mg of the second sample. In the above spectrum, the FID amplification value of the characteristic peak of PbI$_2$(DMSO) confirmed previously was extracted and the result is shown in FIG. 5.

Using the above results. PbI$_2$(DMSO) in the second sample was quantified as shown in Table 3 below.

TABLE 3

| | |
|---|---|
| (C) Molecular weight of PbI$_2$(DMSO) | 539.14238 (g/mol) |
| (D) Molecular weight of Pb(NO$_3$)$_2$ | 331.21 (g/mol) |
| (E) Mass of Pb(NO$_3$)$_2$ | 32 mg |
| (F) Mass of the second sample | 21.36 mg |
| (G) FID amplification value of the second sample | 495.414 |
| (H) FID Amplification value of Pb(NO$_3$)$_2$ | 1250.63 |

Concentration of PbI$_2$(DMSO) in the second sample ((C/D) × (E/F) × (G/H)) = 96.6(wt %)

6) Verification of Quantitative Analysis

In order to verify the results of the above quantitative analysis, the concentration was analyzed by the TGA method described in Science 2015, Vol. 348, no. 6240, pp. 1234-1237.

The TGA method is a method of quantifying the amount of DMSO, and when PbI$_2$(DMSO) and PbI$_2$ were present as in the second sample, quantitative analysis is possible, but when PbI$_2$(DMSO) and PbI$_2$(DMSO)$_2$ were present as in the first sample, it could not be confirmed by which structure the detected DMSO was caused. Therefore, only the second sample was quantified by TGA method, and the result is shown in FIG. 6.

Figure 6:
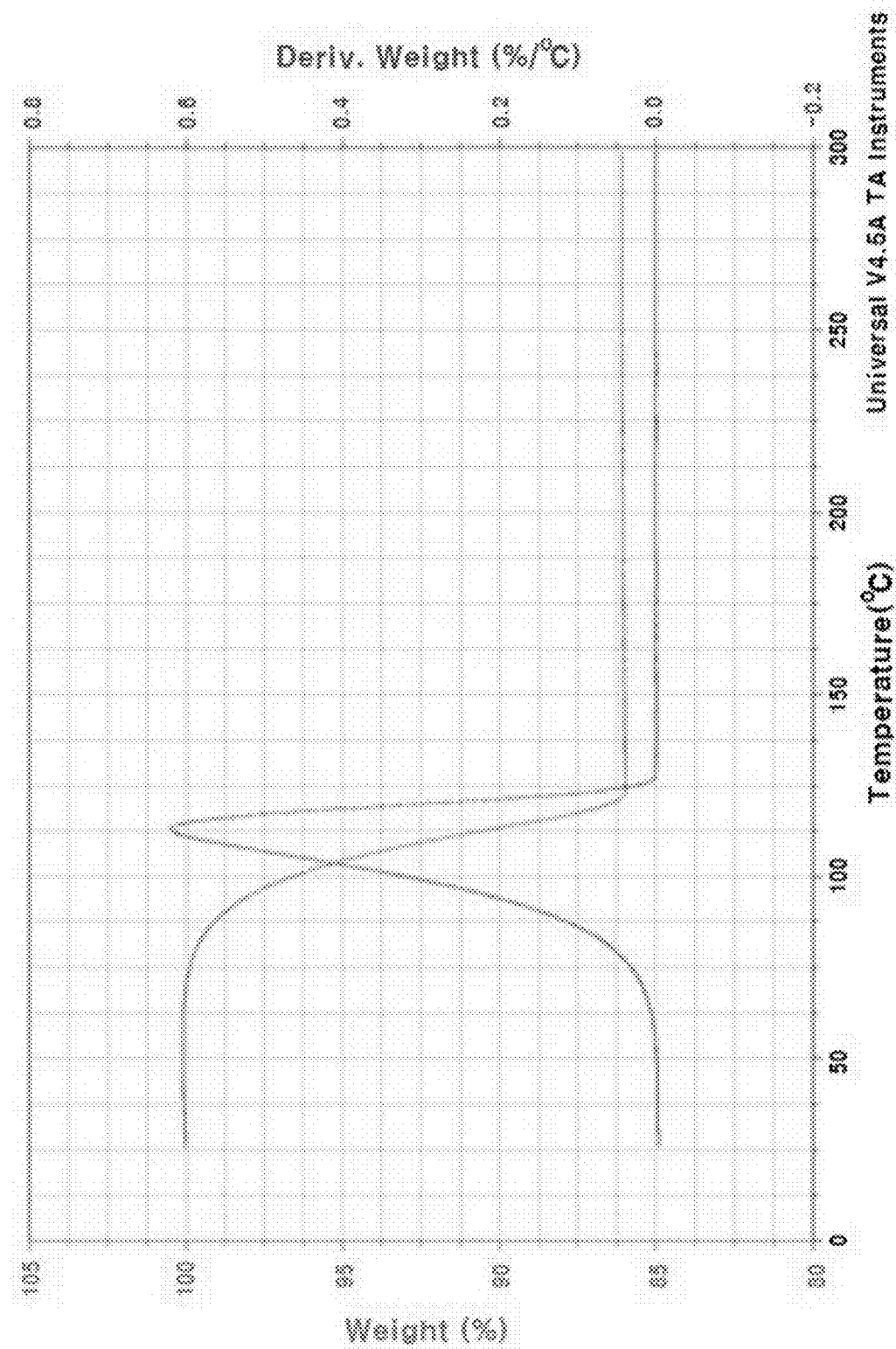
FIG. 6 shows TGA result of the second sample in Example 2 of the present invention.

The results of TGA of the second sample are shown in FIG. 6. Since PbI$_2$ is decomposed above 600° C., the weight reduction up to 300° C. can be assumed to be due to DMSO. The starting mass of TGA was 7.401 mg and the weight reduction up to 300° C. was 1.038 mg. Therefore, the mass of DMSO in the second sample is 1.038 mg, which is 0.000013286 moles when converted to the number of moles (molecular weight of DMSO: 78.13). Since the DMSO in the second sample is present in PbI$_2$(DMSO), the above number of moles is the same as that of PbI$_2$(DMSO), thus yielding 7.163 mg when converting to mass, and the PbI$_2$(DMSO) in the second sample is 96.78 wt % (7.163 mg/7.401 mg).

It could be confirmed that the above quantitative results are very similar to the concentration, 96.6 wt %, of PbI$_2$(DMSO) in the second sample, which was analyzed by the quantification method according to the present invention.

The invention claimed is:

1. A method for quantifying a compound in a sample comprising the steps of:
   1) obtaining NMR spectrum of a standard substance comprising an NMR active atom, and separately obtaining NMR spectrum of the compound under a same condition, wherein the compound comprises the NMR active atom;
   2) obtaining HD (free induction decay) amplification values of characteristic peaks in the NMR spectrum of the standard substance and the NMR spectrum of the sample, respectively; and
   3) comparing the respective FID amplification values to measure a concentration of the compound in the sample using shown in Equation 1 below:

$$\text{Concentration of compound in sample (wt \%)}=(A/B)\times(C/D)\times(E/F)\times(G/H) \quad [\text{Equation 1}]$$

in the Equation 1,
   A is a number of NMR active atoms in a molecule of a standard substance corresponding to the characteristic peak of the above standard substance,
   B is a number of NMR active atoms in a molecule of a compound corresponding to the characteristic peak of the sample,
   C is a molecular weight of the compound,
   D is a molecular weight of the standard substance, E is a mass of the standard substance used to obtain the NMR spectrum of the standard substance,
F is a mass of the sample used to obtain the NMR spectrum of the sample,
G is the FID amplification value of the sample, and
H is the FID amplification value of the standard substance;
and wherein the sample is an insoluble sample.

2. The method for quantifying a compound in a sample according to claim 1,
wherein the NMR active atom is hydrogen, lithium, carbon, fluorine, silicon, phosphorus, lead, or tin.

3. The method for quantifying a compound in a sample according to claim 1,
wherein the same condition is that, when performing NMR measurement, a number of scans, a delay time, a pulse width, a pulse power, a receiver gain, and a spinning rate are the same.

4. The method for quantifying a compound in a sample according to claim 1,
wherein the characteristic peak in the NMR spectrum of the sample is a characteristic peak of a compound contained in the sample.

* * * * *